(12) United States Patent
Khong et al.

(10) Patent No.: US 9,668,791 B2
(45) Date of Patent: Jun. 6, 2017

(54) SURGICAL IMPLANT DEVICE, METHOD AND APPARATUS FOR IMPLANTING THEREOF

(76) Inventors: Kok Sun Khong, Singapore (SG); Rama Krishna Kotlanka, Singapore (SG)

( * ) Notice: Subject to any disclaimer, the term of this patent is extended or adjusted under 35 U.S.C. 154(b) by 162 days.

(21) Appl. No.: 14/388,219

(22) PCT Filed: Apr. 4, 2012

(86) PCT No.: PCT/SG2012/000119
§ 371 (c)(1),
(2), (4) Date: Sep. 25, 2014

(87) PCT Pub. No.: WO2013/151501
PCT Pub. Date: Oct. 10, 2013

(65) Prior Publication Data
US 2015/0038967 A1    Feb. 5, 2015

(51) Int. Cl.
| | | |
|---|---|---|
| *A61B 17/56* | (2006.01) | |
| *A61B 17/72* | (2006.01) | |
| *A61B 17/16* | (2006.01) | |
| *A61B 17/74* | (2006.01) | |
| *A61B 17/17* | (2006.01) | |
| *A61B 17/86* | (2006.01) | |

(52) U.S. Cl.
CPC .......... *A61B 17/725* (2013.01); *A61B 17/164* (2013.01); *A61B 17/1725* (2013.01); *A61B 17/72* (2013.01); *A61B 17/7283* (2013.01); *A61B 17/744* (2013.01); *A61B 17/1668* (2013.01); *A61B 17/1697* (2013.01); *A61B 17/1721* (2013.01); *A61B 17/7241* (2013.01); *A61B 17/863* (2013.01); *A61B 2017/1602* (2013.01)

(58) Field of Classification Search
CPC .... A61B 17/72; A61B 17/7233; A61B 17/725; A61B 17/68; A61B 17/7208–17/7241
USPC ...................................... 606/62–64
See application file for complete search history.

(56) References Cited

U.S. PATENT DOCUMENTS

| | | | | |
|---|---|---|---|---|
| 2007/0123876 A1* | 5/2007 | Czartoski | ............... | A61B 17/72 606/62 |
| 2007/0219636 A1* | 9/2007 | Thakkar | ............. | A61B 17/1721 623/18.11 |
| 2011/0282395 A1* | 11/2011 | Beyar | ................ | A61B 17/1631 606/301 |
| 2012/0221005 A1* | 8/2012 | Corneille | ........... | A61B 17/1631 606/62 |
| 2014/0012259 A1* | 1/2014 | Matityahu | ............ | A61B 17/748 606/62 |

FOREIGN PATENT DOCUMENTS

CN           201551384       *   8/2010   ............. A61B 17/72

OTHER PUBLICATIONS

Machine translation, CN201551384.*

* cited by examiner

*Primary Examiner* — Jacqueline Johanas
*Assistant Examiner* — Tessa Matthews

(57) ABSTRACT

A surgical implant device comprising: a nail, a first locking screw and a second locking screw, each of the first locking screw and the second locking screw are secured near one end of the nail to form an architecture having a substantial triangular shape, a first reinforcing screws being releasably mounted along the length of the nail.

15 Claims, 15 Drawing Sheets

Other Application Sites

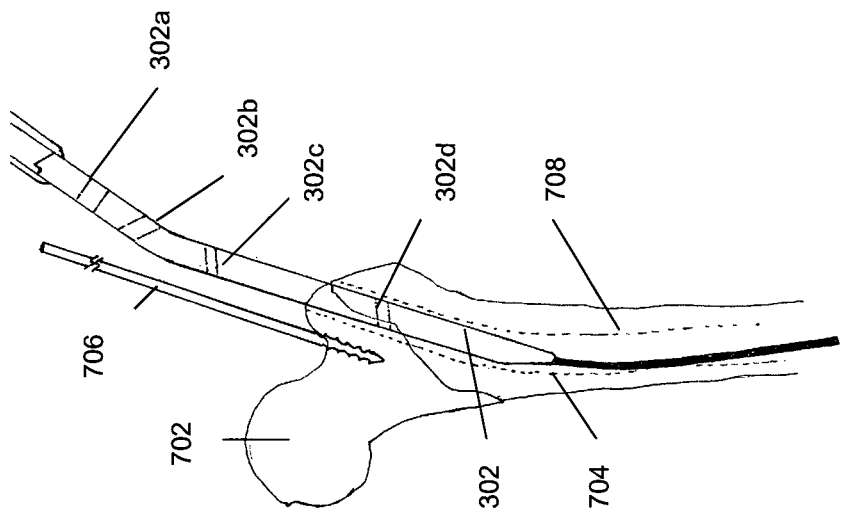
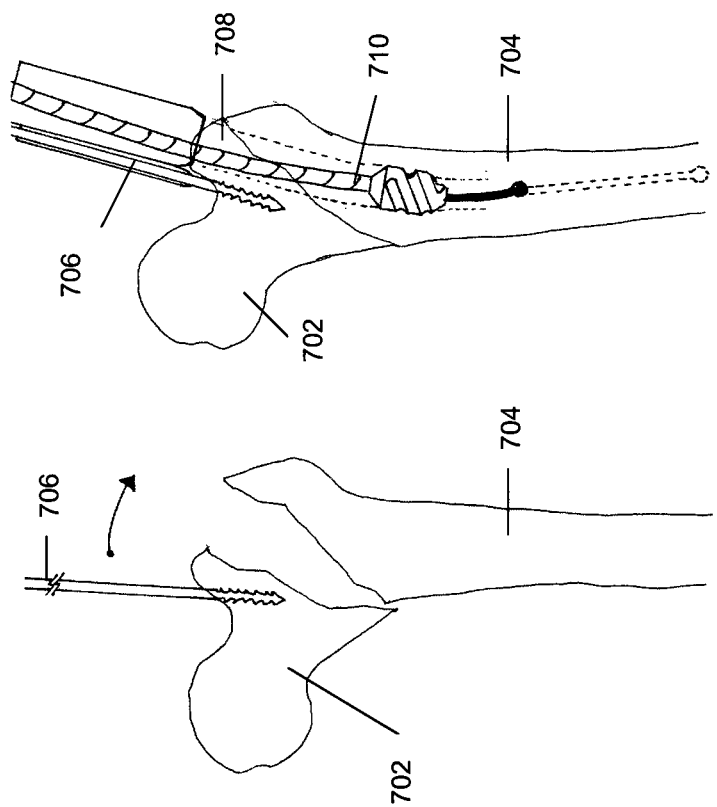
Figure 7C
Figure 7B
Figure 7A

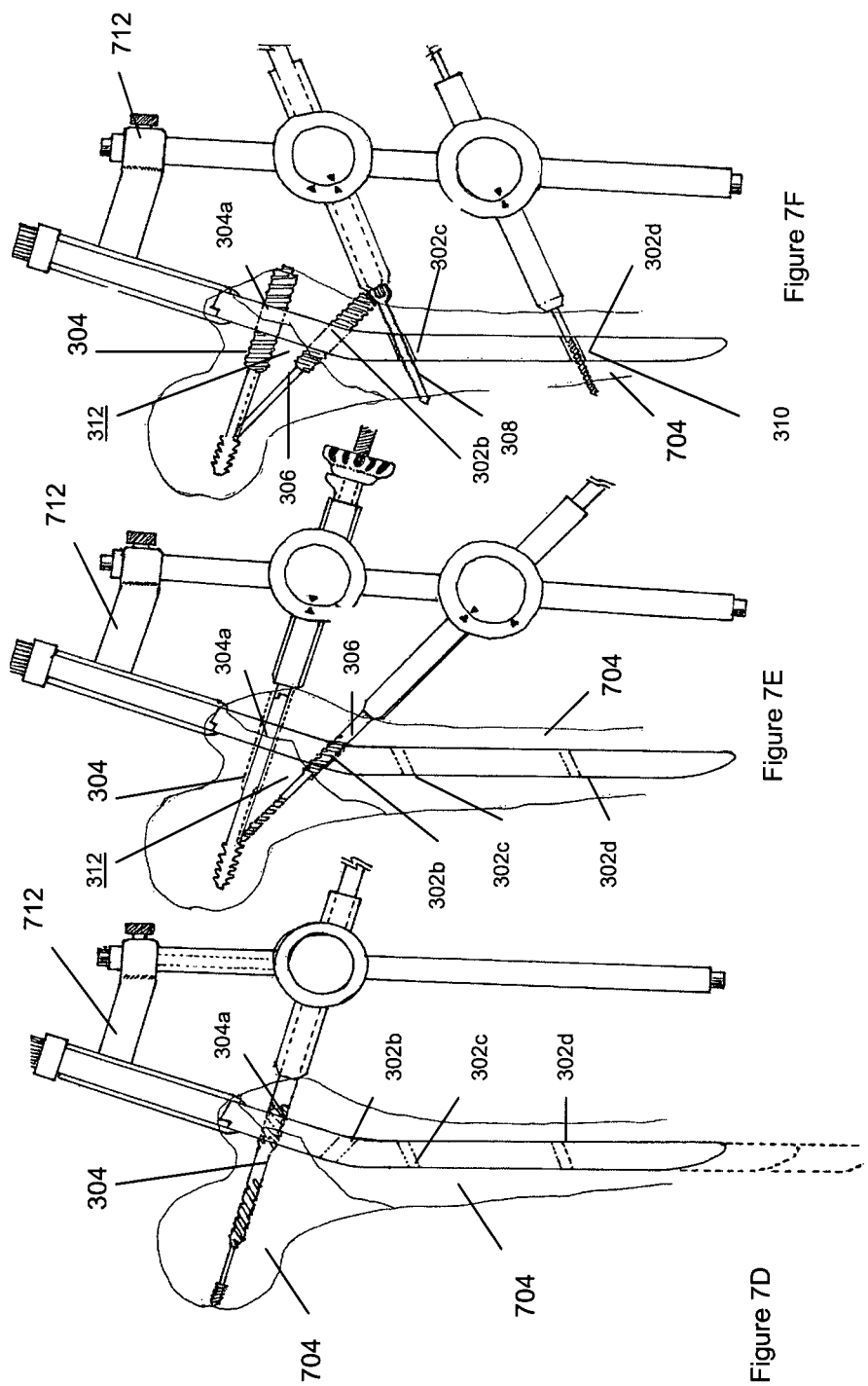

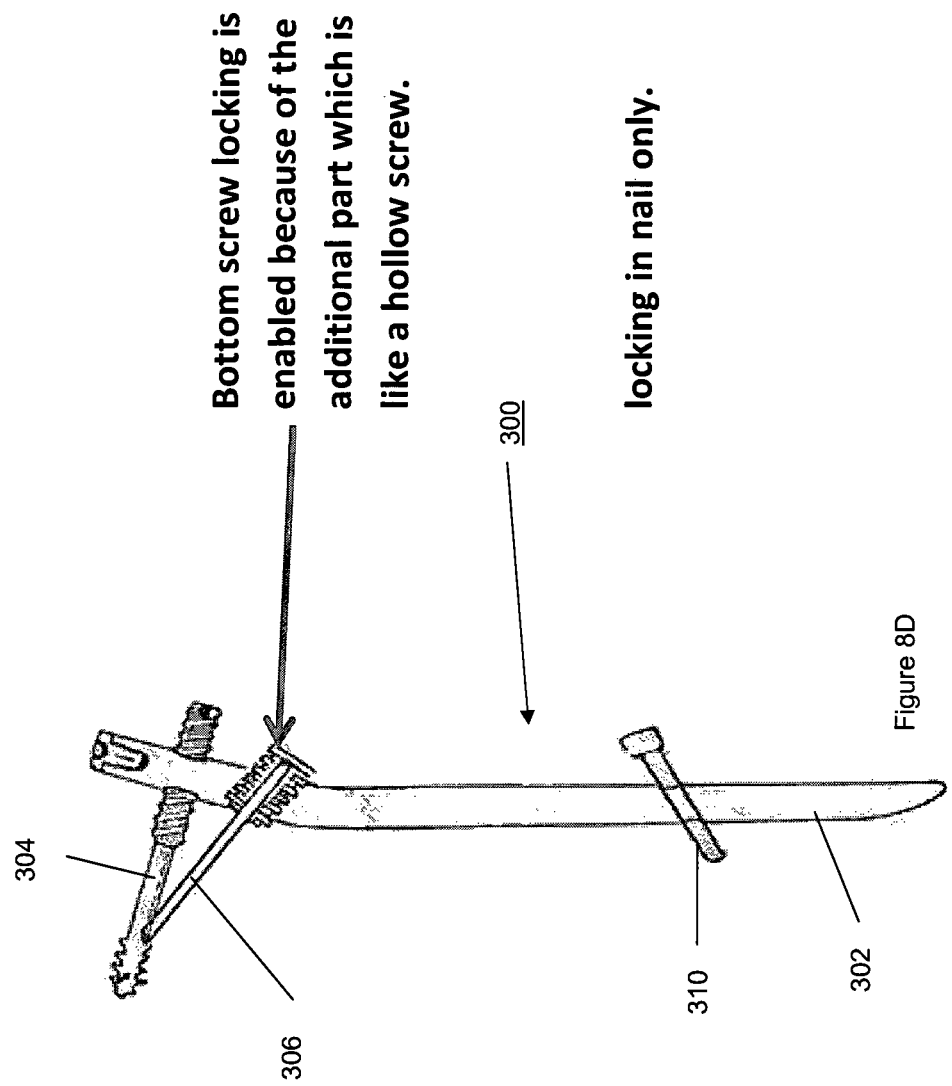

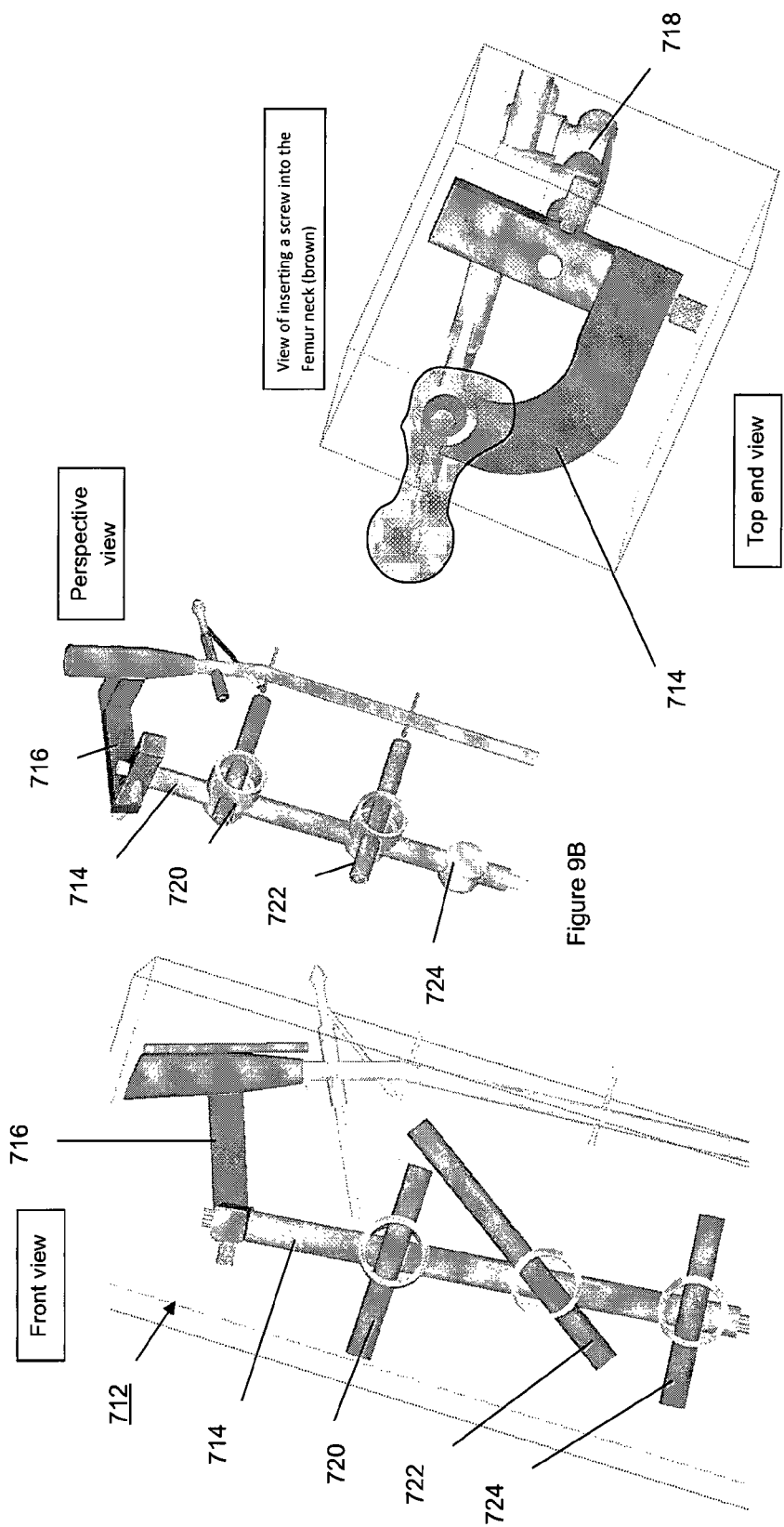

SURGICAL IMPLANT DEVICE, METHOD AND APPARATUS FOR IMPLANTING THEREOF

This is a U.S. national phase non-provisional utility patent application claiming priority to and the benefit of PCT international application no. PCT/SG2012/000119, filed on Apr. 4, 2012, currently pending, which is incorporated herein by reference in its entirety.

FIELD OF THE INVENTION

The present invention relates to a surgical implant device utilised by surgeons to treat or reconstruct fractured bone in trauma situations. It also relates to the method of implanting the surgical implant device into the fractured bone and the apparatus used to implant the surgical implant device into the fractured bone.

BACKGROUND

Various devices and methods have been used in the prior art for the fixation of bones or bone portions. In the case of procedures wherein the fixation of delicate bones is required, fine metallic wires are secured through holes drilled in the bones. Wires and pins of somewhat greater diameter can also be inserted through the bones with an apparatus such as a wire driver which resembles a rotary power drill. Staples have been employed as well to fixate osteotomy sites. In the case of larger bones, particularly in the reduction of fractures, self-tapping bone screws are often inserted into drill holes to secure portions of the bone on either side of the fracture and enable healing to occur.

Where greater stabilization is required or where in the case of a fracture, for example, a substantial amount of stress will be placed on the fragmented bone portions because of the position of the fracture, the weight of the patient, the nature of athletic or other activity in which the patient wishes to engage, or similar factors, bone-fixating compression plates are often placed across the fracture line and are anchored by screws inserted through the plates and into the bone on either side of the fracture.

In the open reduction and minimally invasive internal fixation of a variety of fractures of the proximal femur and femoral neck, combination screw and plate devices have been utilized wherein a cavity in the femoral neck is reamed out and a plate is put against the outer surface of bone through which a large screw or bolt is inserted and screwed into the reamed-out cavity. The screw or bolt is attached to a plate which abuts against the cortex of the femur. The plate is anchored in the bone by smaller bone screws.

The use of prior art devices such as screws or screw and plate combinations where compression of bone portions, for example in the case of fractures, is required, has significant drawbacks. Bone screws are normally inserted through the cortex of a bone and secured in the relatively soft bony material in the medulla, and the primary compressing force is provided by threads of the screw gripping into the medulla and the head of the screw pressing against the cortex. Particularly in the case of osteoporotic bone, the bone screws frequently do not provide sufficient compression on the bone to reduce the fracture properly.

In addition, when bone screws are used, even in cases where the opposite cortex is purchased, a very large hole is created through the cortex and medullary bone which cannot be filled in with bony material while the screw is in position. If the screw is removed, the areas of the bone immediately surrounding the screw hole have a greater susceptibility to cracking or fracturing than normal bone, and the bone is not filled in by natural healing processes for a considerable amount of time.

An example of a prior art device 100 is shown in FIG. 1. The prior art device 100 includes a nail-hip screw system whereby a nail 102 is inserted down the femur shaft. One or two gliding screws 104a, 104b are inserted into the femoral neck at 130°. Thus, the gliding screws 104a, 104b are positioned in parallel to each other and do not engage with each other.

Another example of a prior art device 40 is shown in FIG. 2. The prior art device 40 includes a bone plate 42 secured to the bone 44 by screws 46a to 46f, which are inserted through holes in bone plate 42 and into the bone about fracture 47 to hold the fragments of bone 44 in place until bone 44 heals. Bone plate 42 is shown as a blade plate, including plate portion 48 having a plurality of holes there through for receipt of screws 46a to 46f, and blade portion 50 extending from plate portion 48 to define an angle there between. Plate portion 48 and blade portion 50 are connected at bend 52, which defines fillet radius intermediate plate portion 48 and blade portion 50. It may be seen that, due to the large size of fillet radius (non conformal shape of the bone), a large gap 56 exists between plate portion 48 and outer surface 58 of bone 44 adjacent bend 52, wherein bend 52 projects outwardly of outer surface 58 of bone 44. Screws 46a to 46f include strut screw 46c, which is disposed through one of the holes in plate portion 48 and extends towards blade portion 50 of blade plate 42 such that end 60 of strut screw 46c abuts blade portion.

It is an object of the present invention to provide a surgical implant device having screws that can cater for combined loading (axial, bending and tension) and mimic nature's way of load transfer via the trabecular pattern of bone.

It is another object of the present invention to reduce the implant material thus becoming "Mini-Max" implant, due to the locking nature of the screws and the load being shared among all parts of the implant.

It is yet another object of the present invention to reduce the "Z-type" failures sometimes seen in other intramedullary implants. This unique type of failure results from differential fixation stability of two diameters of parallel screws into a femoral neck subject to oscillating motion during the recovery period.

Other objects and advantages of the present invention will become apparent from the following description, taken in connection with the accompanying drawings, wherein, by way of illustration and example, an embodiment of the present invention is disclosed.

SUMMARY OF THE INVENTION

In accordance with a first aspect of the invention, there is provided a surgical implant device comprising:
 a nail,
 a first locking screw and a second locking screw,
  each of the first locking screw and the second locking screw are secured near one end of the nail to form an architecture having a substantial triangular shape,
 a first reinforcing screws being releasably mounted along the length of the nail.

In accordance with a second aspect of the invention, there is provided a method of implanting a surgical implant device into a fractured bone, the bone having two or more fragments due to fracture, the method comprising:
 providing a pin, inserting the pin partially into a fragment of the bone,
using the pin to reduce the fracture by re-engaging the fragment with the corresponding fragment,
drilling a hole through the fragment and partially into the corresponding fragment,
providing a nail having several holes therein,
inserting the nail into the drilled hole in the fragments,
providing a first locking screw and a second locking screw,
disposing each of the first locking screw and second locking screw through one of the holes by means an installing apparatus and extend such that both of the screws engage each other at a position so as to form an architecture having substantial triangular shape,
providing a first reinforcing screw, and
disposing the first securing screw through one of the holes of the nail by means of the installing apparatus.

In accordance with a third aspect of the invention, there is provided an instrumentation device for installing the surgical implant device into the fractured bone, comprising:
an elongated frame,
a securing mechanism releaseably mounted on one end of the frame, the securing mechanism capable of inserting a nail into the bone,
one or more securing mechanism pivotally mounted along various location of the frame, the securing mechanism capable of inserting screws into the bone.

BRIEF DESCRIPTION OF THE DRAWINGS

By way of example/illustration only, an embodiment of the invention is described more fully hereinafter with reference to the accompanying drawings, in which:

FIGS. 7A to 7F shows the method of implanting a surgical implant device 300 into the fractured bone (in this case the proximal femur bone).

FIG. 8A to 8E shows different embodiments of the interlocking between the nail, the top locking screw and the bottom locking screw which result in the formation of an architecture having a substantial triangular shape.

FIGS. 9a to 9c shows different views of the installing instrument 712.

DETAILED DESCRIPTION

Figure 3:
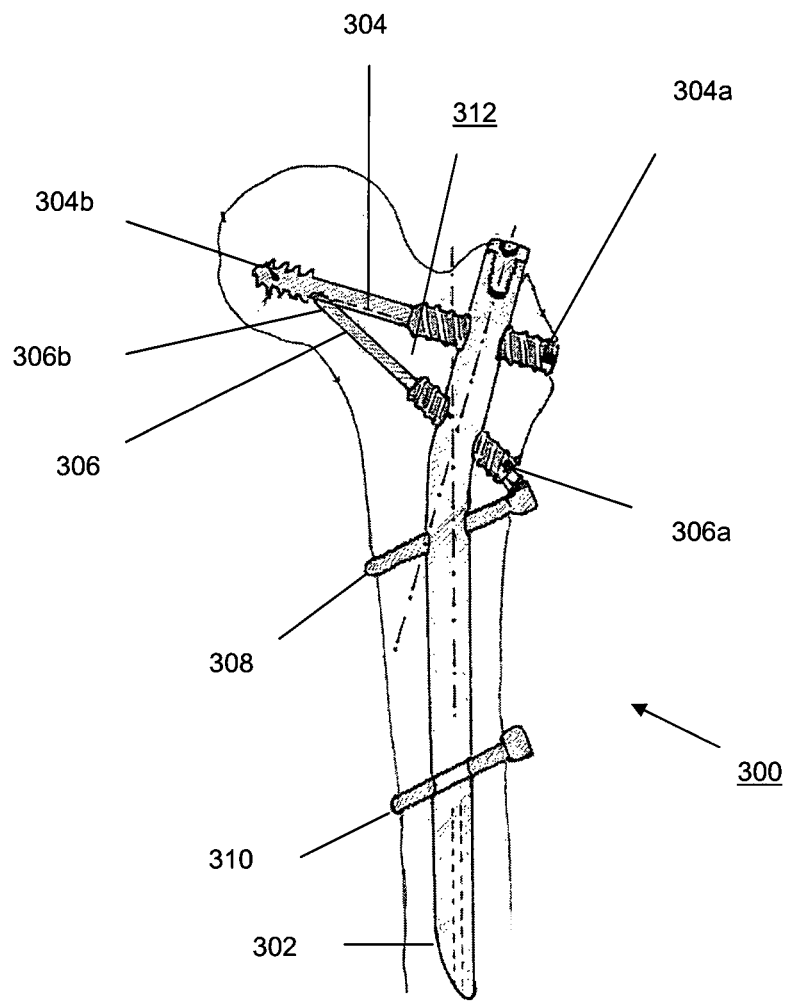
FIG. 3 shows the surgical implant device 300 in a preferred embodiment of the present invention.

FIG. 3 shows the surgical implant device 300 adapted to treat or reconstruct fractured bone in trauma situation in a preferred embodiment of the present invention.

As shown, the surgical implant device 300 includes a nail 302. A first locking screw 304 and a second locking screw 306 are secured near one end of the nail 302 to form an architecture 312 having a substantial triangular shape.

The nail 302 may be in the form of intramedullary nail or Z-LOC petrochanteric nail and may have a diameter from 10 to 16 mm. The nail 302 may have an end cap at one end and a convex distal taper with a diameter of 10 mm to 12 mm at the other end. The first locking screw 304 may be in the form of lag screw and the second locking screw 306 may be in the form known as a "Ward strut" to engage with the first locking screw 304.

In the event of breakage of the locking screws, removal of the locking screws can be extremely difficult. Thus, it is important to make sure the locking screws are made of good quality material. In the preferred embodiment, the nail 302 and the locking screws 304, 306 are made of biocompatible material. Some examples of biocompatible material include stainless steel 316L/322, pure titanium, titanium alloys, alloys, cobalt and its alloy, carbon fiber reinforced polymers.

The first locking screw 304 with large cancellous far thread 304b has a threaded sleeve 304a adapted to interlock with the nail 302. The first locking screw 304 may have a core diameter of 8 mm and a diameter of 12 mm at the far threaded surface 304b. The threaded sleeve 304a is adapted to secure the first locking screw 304 after the first locking screw 304 is disposed through one of the holes of the nail 302. This is a form of "interference-fit". The second locking screw 306 has only a threaded surface 306a at one end and a round tip 306b at the other end. The second locking screw 306 may have a diameter of 6 mm. The threaded surface 306a may also known as sleeve 306a and may be used to secure the second locking screw 306 when the second locking screw 306 is disposed through one of the holes in the nail 302. The position of the nail 302 within the bone is reinforced with a reinforcing screw 310 releasably mounted along the length of the nail 302. The reinforcing screw 310 is disposed through one of the holes in the nail 302. The hole may be in the form of an oval-shaped slot which allows the nail 302 to glide vertically up to 5 millimeters within the bone. A second reinforcement screw 308 may be releasably mounted along the length of the nail between the first reinforcing screw 310 and the second locking screw 306 in an embodiment of the present invention. The second reinforcement screw 308 is disposed through one of the holes in the nail 302. The hole may be in the form of round-shaped hole. More other embodiments are shown in FIG. 8A to 8F which will be described later.

The nail 302 is provided with several holes for receipt of the screws. Each of the first locking screw 304 and the second locking screw 306 are disposed through one of the holes and extend such that both of the locking screws engage each other at a position so as to form an architecture 312 having a substantial triangular shape. The threaded surface 304b of the first locking screw 304 engage with the round tip 306b of the second locking screw 306.

Figure 1:
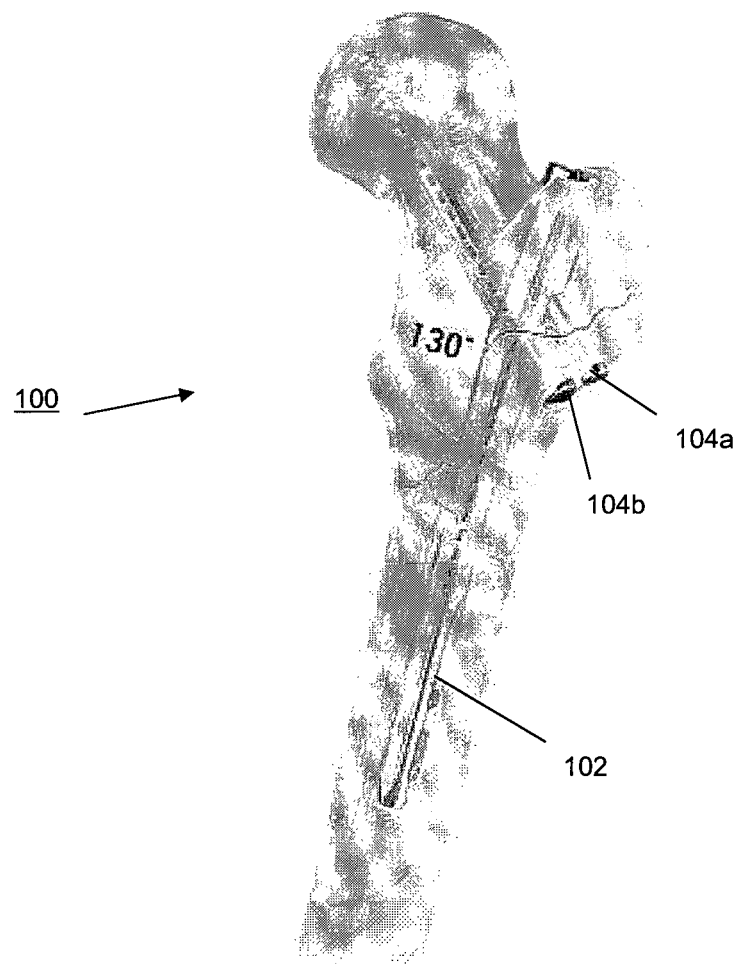
FIG. 1 shows an example of a prior art device 100.
Figure 2:
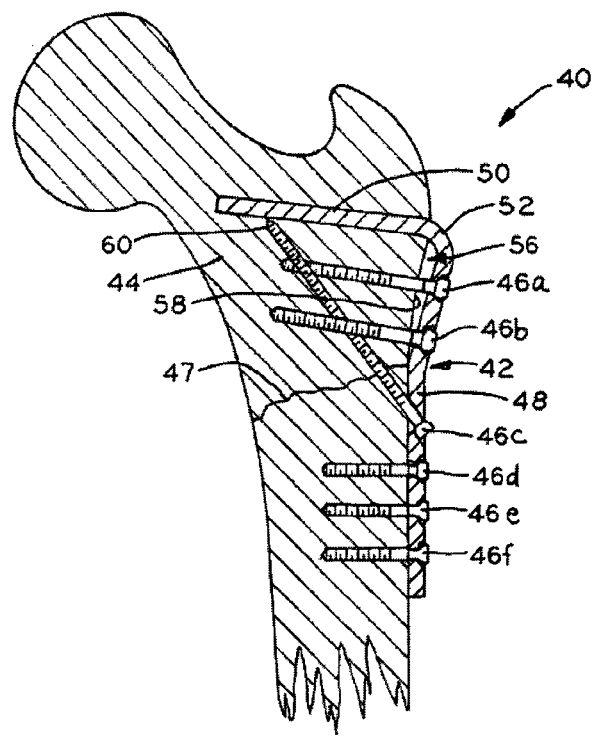
FIG. 2 shows another example of a prior art device 40.

Due to the formation of the architecture 312 having a substantial triangular shape (also known as "Ward's triangle"), the first locking screw 304 and the second locking screw 306 complement each other in load transfer and thus effectively reduce the usage of the implant material, that is "Mini-Max" fixation. "Mini-Max" fixation is defined herein as the minimal implant material for maximum strength. The architecture of the fixation also allows the surgeon to exploit placing the locking screws 304, 306 close to the cortical bone. Experiment has shown that this would reduce the emphasis of special lag screw (see FIG. 1) that is currently used to hold the femur head in cancellous bone. Furthermore, the locking screws 304, 306 are used to provide necessary strength to the fixation. Furthermore, due to the thin diameter of the locking screws 304, 306, damage to the bone due to screw insertion would be minimised.

Reinforcing screw 310 is releasably mounted along the length of the nail. An second reinforcing screw 308 may also be releasably mounted along the length of the nail between the first reinforcing screw 310 and the second locking screw 306 in an embodiment of the present invention. When in use, each of the reinforcing screws 308, 310 are disposed through to one of the holes of the nail 302 in, order to secure the nail 302 along the length of the bone in an embodiment of the present invention. The first reinforcing screw 310 may be in the form of shaft derotation screw having a diameter of 4.5 mm and the second reinforcing screw 308 may be in the form of subtrochanteric screw having a diameter of 4.5 mm. Those skilled in the art will recognise that the number of reinforcing screws will depend on the severity of the fracture and the depth of the penetration of the nail in the femur bone.

The engagement of the first and second locking screws 304, 306 is crucial in order for the surgical implant device 300 to achieve its function. Due to the engagement of the first and second locking screws 304, 306, both of the locking screws 304, 306 share the load originating from the femur head and transfer the load onto the nail 302 in the form of medullary nail. At the same time, backing or pullout of the locking screws 304, 306 would not occur as they are interlocked in an architecture 312 having a substantial triangular shape. A reinforcing screw 310 is releasably mounted at an inclination on the nail 302 to provide stability for all primary loading conditions like compression, bending and torsion or a combination of primary loads. In addition, that first reinforcing screw 310 is disposed through one of the holes in the nail 302. The hole may be in the form of oval-shaped slot which allows the nail 302 to glide vertically within the bone of up to 5 millimeters. A second reinforcing screw 308 may be releasably mounted along the length of the nail between the first reinforcing screw 310 and the second locking screw 306 in an embodiment of the present invention. The second reinforcement screw 308 is disposed through one of the holes in the nail 302. The hole may be in the form of round-shaped hole.

Figure 4C:
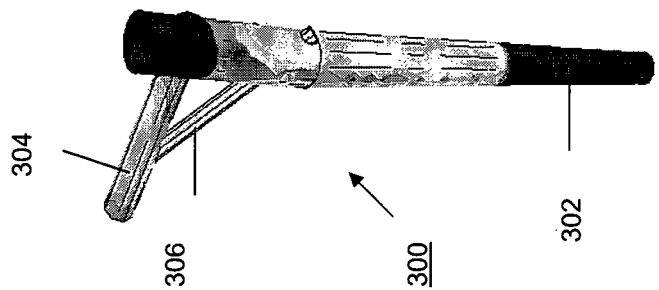
FIG. 4C shows the prototype (stress contour of the present invention for physiological loading condition, single leg stance loading condition) of the surgical implant device 300 in a preferred embodiment of the present invention.
Figure 4B:
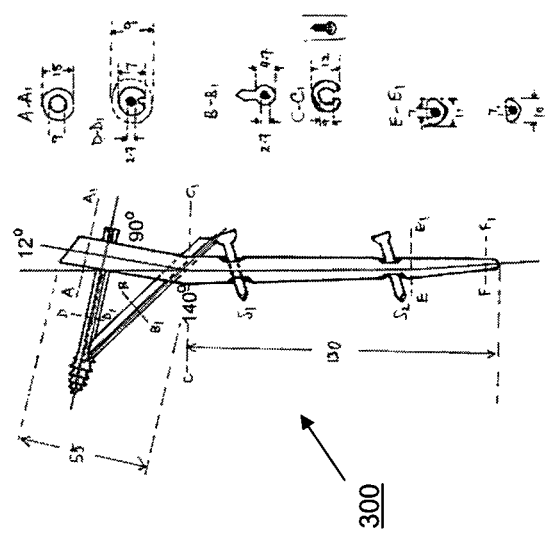
FIG. 4B shows the dimension of the surgical implant device 300 in a preferred embodiment of the present invention.
Figure 4A:
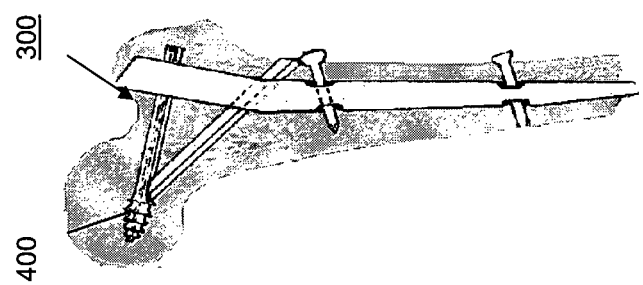
FIG. 4A shows the surgical implant device 300 being implanted within the proximal femur bone 400.

FIG. 4A shows the surgical implant device 300 being implanted within the proximal femur bone 400.

FIG. 4B shows the dimension of the surgical implant device 300 in a preferred embodiment of the present invention. It will be understood that dimensions are for illustration purposes only and other dimensions of the surgical implant device 300 is also possible.

FIG. 4C shows finite element simulation and the stress pattern of the surgical implant device 300 having the first locking screw 304 with diameter bigger than the diameter of the second locking screw 306.

Figure 5B:
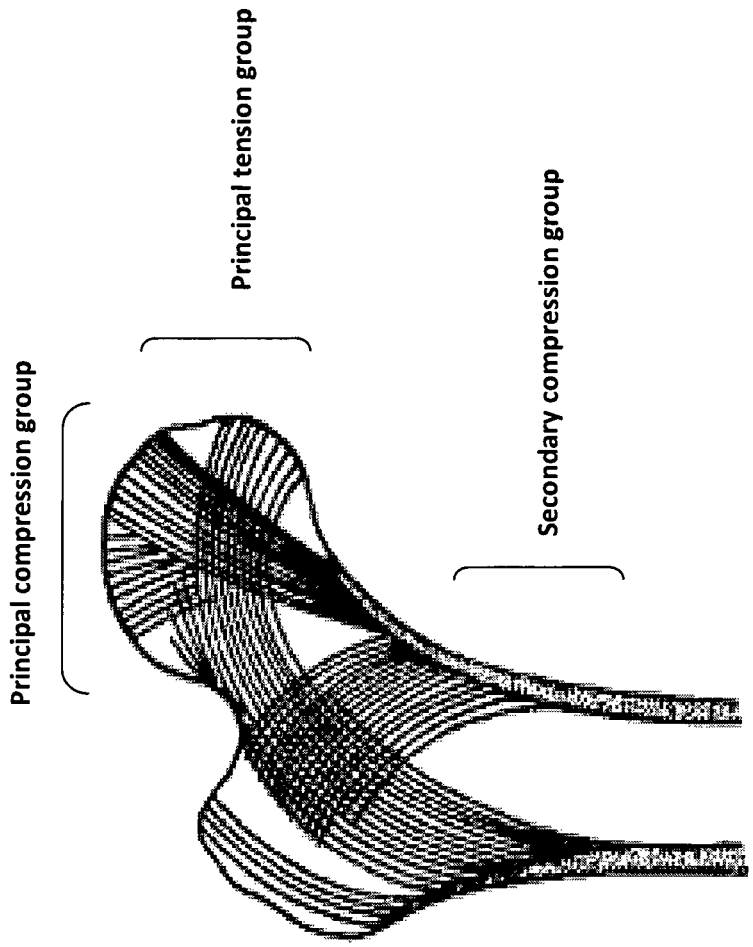
FIG. 5B shows the femur bone depicting the known stress trajectories to transfer the load from proximal femur bone to distal femur bone with the surgical implant device 300. The surgical implant follows the stress trajectories for load transfer from proximal femur bone to distal femur bone.
Figure 5A:
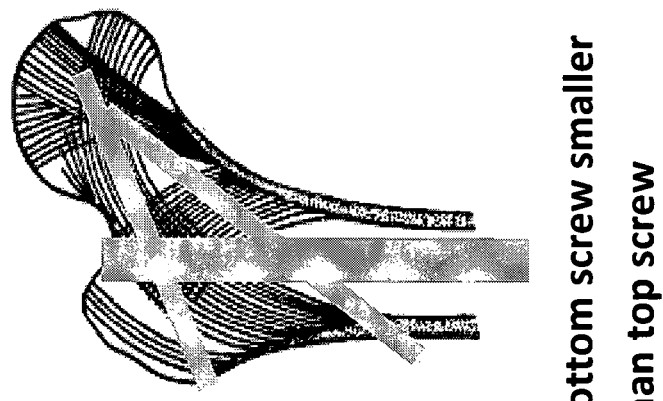
FIG. 5A shows the femur bone depicting the known stress trajectories to transfer the load from proximal femur bone to distal femur bone.

Computer stimulation on the conceptual design of the surgical implant device 300 has been performed. Computer stimulation includes finite element analysis. Data results from the computer simulation show that the first locking screw 304 is primarily subjected to a combined load (bending and tension) while the second locking screw 306 is subjected to compressive load. Such results are in accord with the stress trajectories in the bone (in this case the femur bone) as shown in FIGS. 5A and 5B which depict the known stress trajectories to transfer the load from proximal femur bone to distal femur bone with the surgical implant device 300. In particular, FIG. 5A shows the femur bone depicting the known stress trajectories to transfer the load from proximal femur bone to distal femur bone and FIG. 5B shows the femur bone depicting the known stress trajectories to transfer the load from proximal femur bone to distal femur bone with the surgical implant device. The surgical implant follows the stress trajectories for load transfer from proximal femur bone to distal femur bone. The surgical implant device 300 has been shown to simulate "ward's triangle" and the stress distribution in the surgical implant device 300 will be similar to Nature's design of the femur bone as shown in FIGS. 5A and 5B.

The surgical implant device 300 can be used by surgeons to treat or reconstruct proximal (upper) femur bone fractures by implanting a first locking screw 304 which act as an interlocker to provide more stability and also to reduce the load on the primary load bearing/sharing screw as shown in FIG. 5B. The surgical implant device 300 has been shown to simulate "ward's triangle" and the stress distribution in the surgical implant device 300 will be similar to Nature's design of the femur bone as shown in FIG. 5A. It is submitted that such application is able to reduce the failure of the surgical implant device 300. The surgical implant device 300 is designed to improve and enhance treatment with mechanobiological concepts, rather than purely mechanical concept.

Figure 5C:
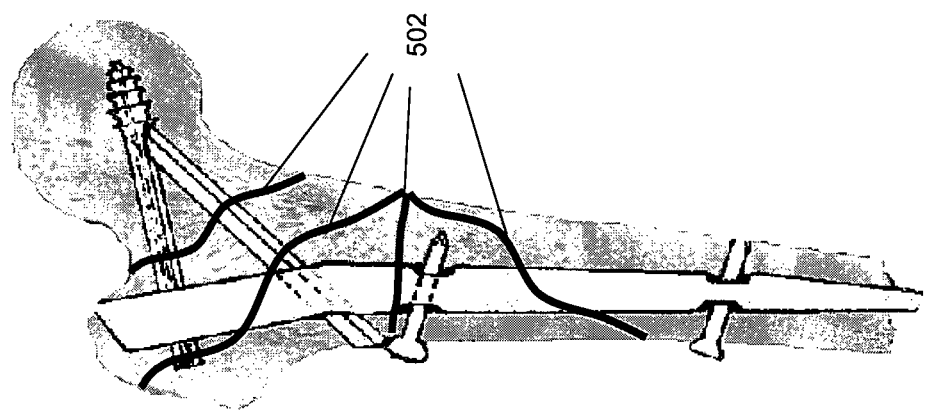
FIG. 5C shows the possible fracture sites in the proximal femur addressed by the application of the surgical implant device 300.

FIG. 5C shows the possible fracture sites 502 in the proximal femur bone which is addressed by the application of surgical implant device 300 inside the proximal femur bone.

Figure 6B:
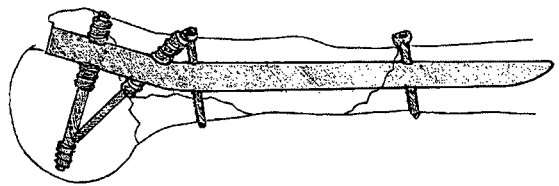
FIGS. 6A and 6B shows the application of surgical implant device in other parts of the skeleton.
Figure 6A:
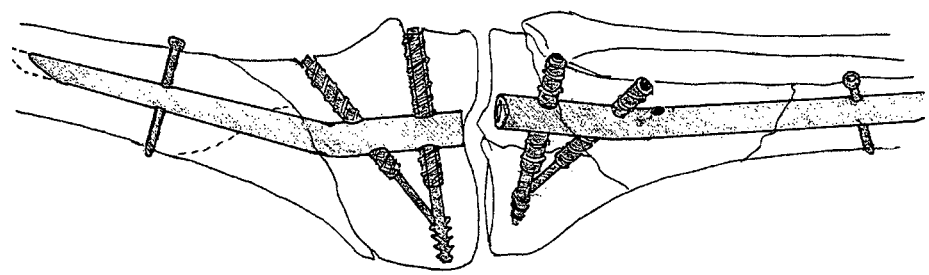

The application of surgical implant device 300 is not restricted to only femur bone. For instance, the surgical implant device can be modified for application to other parts of the skeleton, such as the distal (lower) femur (FIG. 6A), the upper tibia (FIG. 6A) and the proximal (upper) humerus bones (FIG. 6B). The design and structure is the same, but the dimensions may be modified to accommodate the anatomical constraints in these other bones.

The installation of the first and the second locking screws 304, 306 requires an installing apparatus in the form of precision jigs and instrumentation.

FIGS. 7A to 7F shows the method of implanting a surgical implant device 300 into the fractured bone (in this case the femur bone). The fractured bone comprises of two or more fragments as a result of the fracture.

FIG. 7A shows a threaded pin 706 adapted to be inserted partially into one of the fragments 702 of the fractured bone. After the pin 706 is inserted partially into the fragment 702, the pin 706 is used to reduce the fracture by re-engaging the fragment 702 with the corresponding fragment 704.

A hole 708 is then drilled by a drilling rod 710 through the first fragment 702 and partially into the corresponding fragment 704 as shown in FIG. 7B. The standard motorised reaming rod 710 is inserted over a guide rod.

After a hole 708 is formed, a drilling rod 710 is removed and a nail 302 is inserted into the hole 708 as shown in FIG. 7C. The nail 302 may be in the form of Z-LOC nail. The nail 302 is provided with holes 302a to 302d for receipt of the screws. A first locking screw 304 is adapted to be implanted into the fractured bone by being disposed through to one of the holes 302a by means of the installing apparatus 712 using a step-drill as shown in FIG. 7D.

A second locking screw 306 is adapted to be implanted into the fractured bone by being disposed through to one of the holes 302b by means of the installing apparatus 712 using a step-drill as shown in FIG. 7E.

Both of the locking screws 304, 306 extend such that both of the locking screws engage each other at a position so as to form an architecture 312 having a substantial triangular shape, which may also known as "Z-LOC".

Reinforcing screws 308, 310 are adapted to secure the nail 302 along the length of the bone. The first reinforcing screw 310 may be in form of shaft derotation screw and the second reinforcing screw 308 may be in the form of subtrochanteric screw. As shown in FIG. 7F, the reinforcing screws 308, 310 are implanted into the fractured bone by being disposed through the holes 302c, 302d respectively by means of the installing apparatus 712 as shown in FIG. 7F.

Figure 8A:
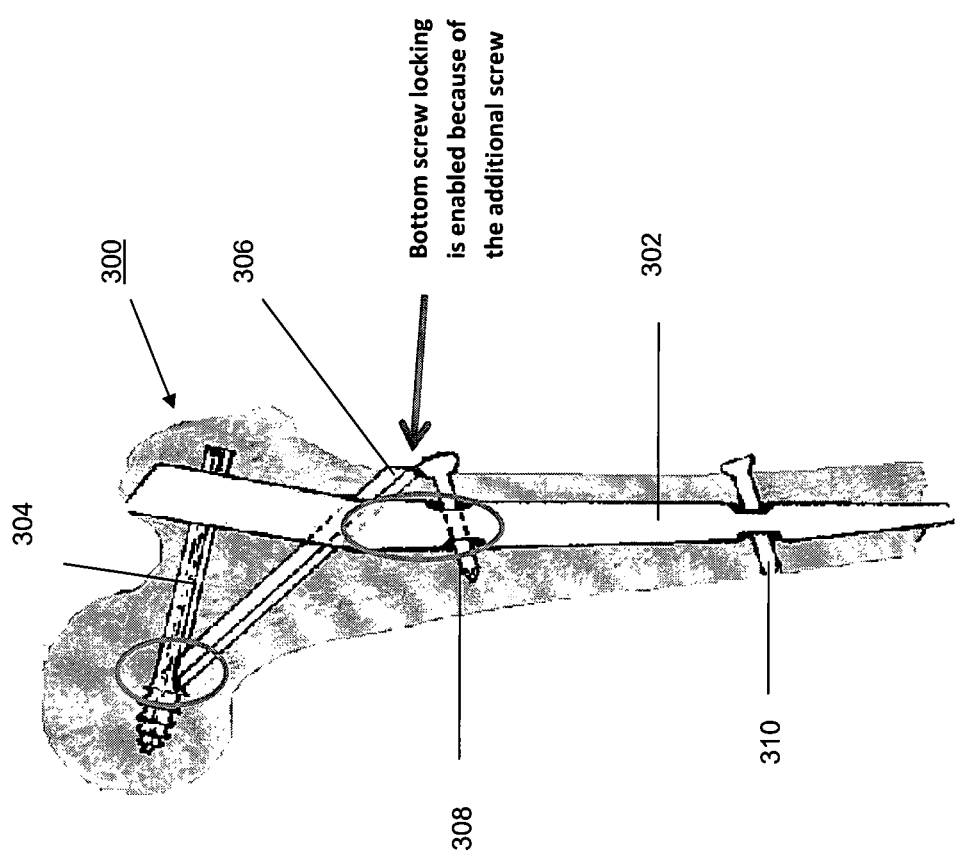

FIG. 8A shows the interlocking region of the surgical implant device 300 in a first embodiment of the present invention. In this embodiment, the position of the second locking screw 306 is reinforced by abutting with a second reinforcing screw 308.

Figure 8B:
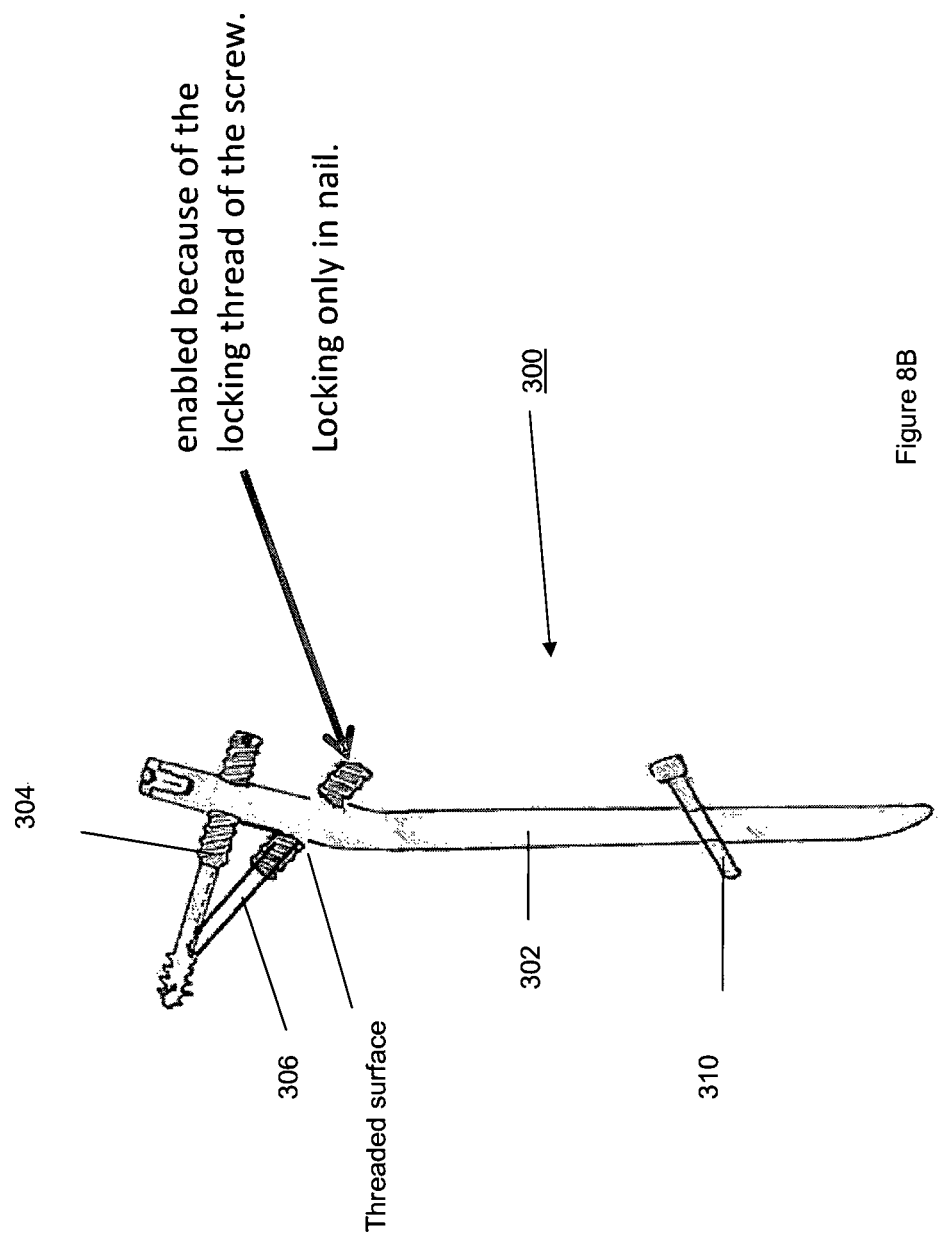

FIG. 8B shows the interlocking region when the surgical implant device 300 in a second embodiment of the present invention. In this embodiment, the position of the second locking screw 306 is reinforced by engaging the threaded surface with one of the holes in the nail 302.

Figure 8C:
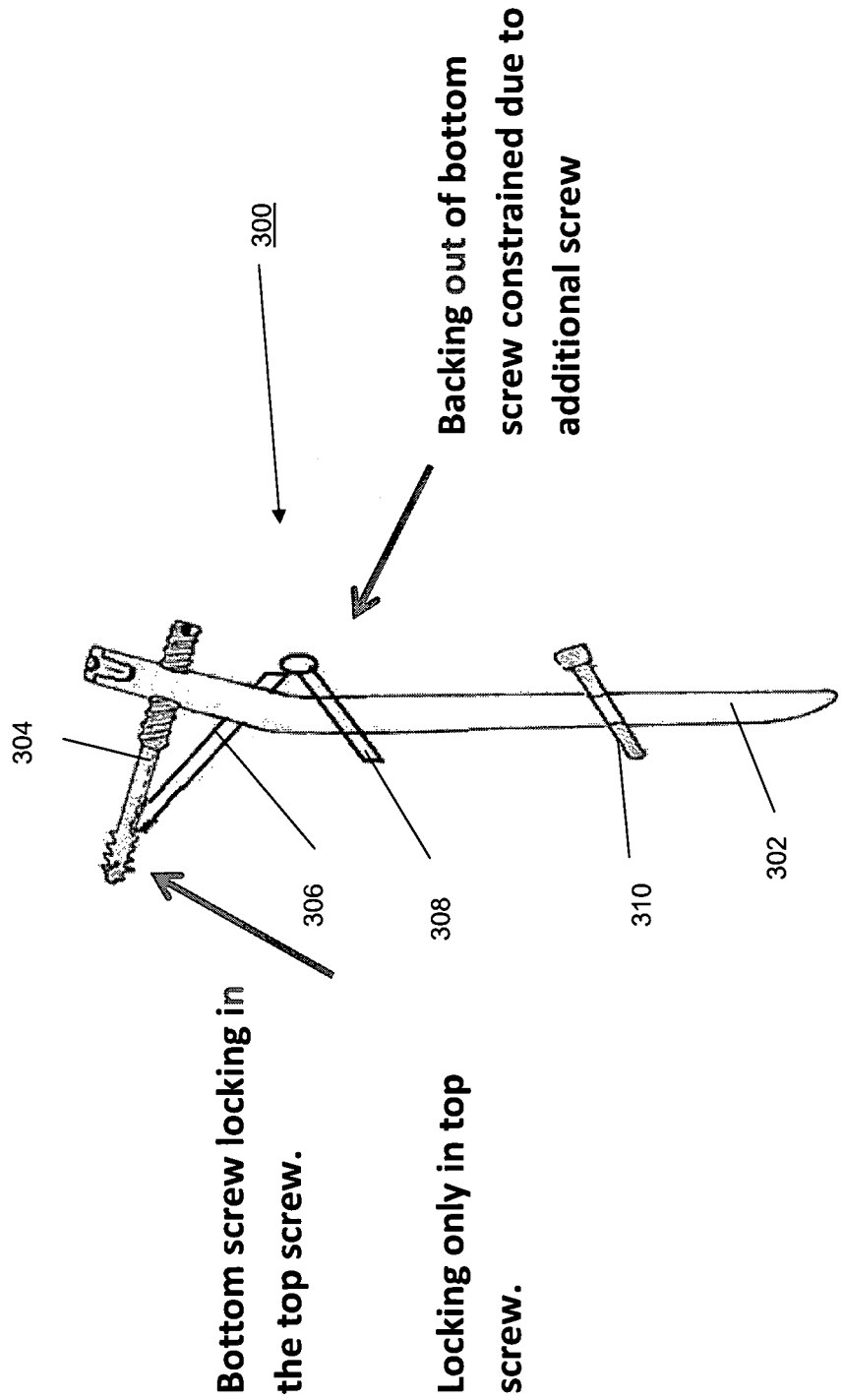

FIG. 8C shows the interlocking region of the surgical implant device 300 in a third embodiment of the present invention. In this embodiment, the position of the second locking screw 306 is reinforced by engaging with the threaded surface of the first locking screw 304 at one end and abutting with the second reinforcing screw 308 at the other end.

FIG. 8D shows the interlocking region of the surgical implant device 300 in a fourth embodiment of the present invention. In this embodiment, the position of the second locking screw 306 is reinforced by screwing a bottom screw at one end.

Figure 8E:
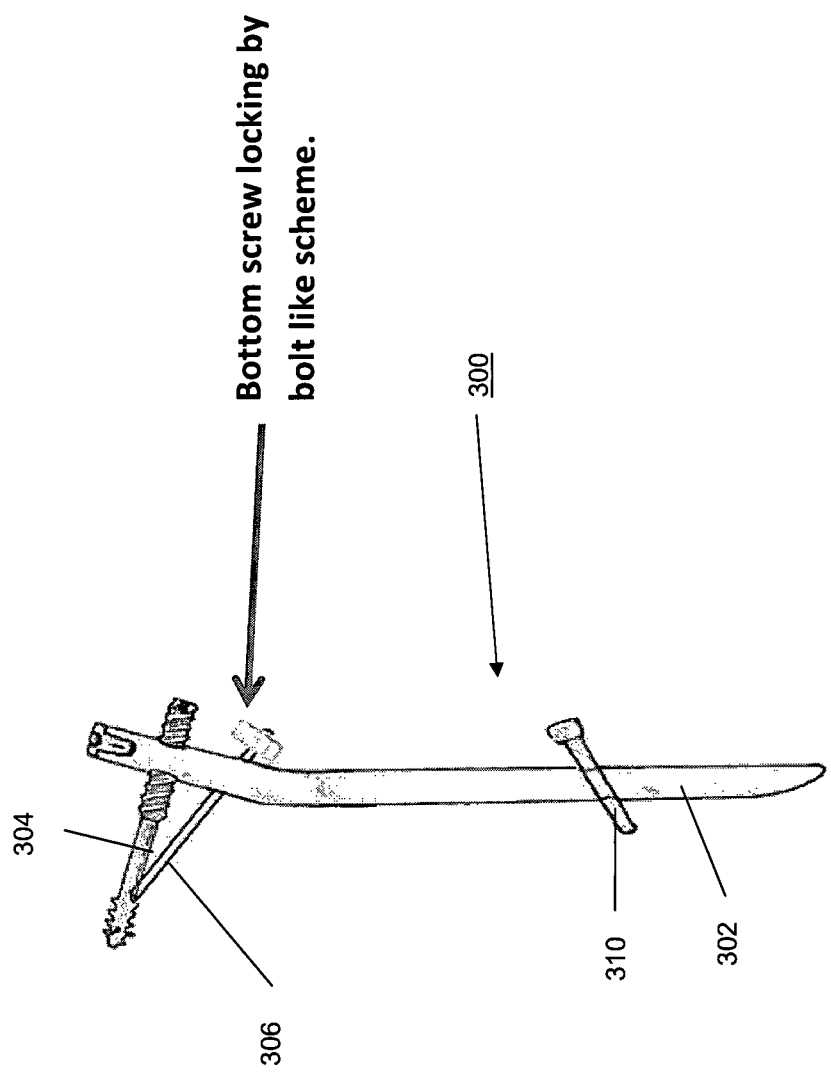

FIG. 8E shows the interlocking region of the surgical implant device 300 in a fifth embodiment of the present invention. In this embodiment, the position of the second locking screw 306 is reinforced by screwing a bolt at one end.

It is submitted that the interlocking region of the surgical implant device 300 is not restricted by the configuration shown in FIGS. 8A and 8E.

FIGS. 9a to 9c shows top view, the perspective view and top end view respectively of the installing device 712 in the form of precision jigs and instrumentation.

The installing device 712 includes an elongated rod 714 with securing members 716, 720, 722, 724 pivotally mounted along its length. One of the securing members 716 which is pivotally mounted near the end of the elongated rod 714. The securing member 716 is adapted to implant the nail 302 into the bone. The other securing members 720, 722, 724 are adapted to implant the screws 304, 306, 308, 310 respectively into the bone.

While the invention has been particularly shown and described with respect to a preferred embodiment thereof, it will be understood by those in the art that various changes in form and details can be made therein without departing from the spirit and scope of the invention.

The invention claimed is:

1. A surgical implant device comprising:
   a nail including
      a vertical axis centrally aligned through a major longitudinal length of the nail, and
      a horizontal axis registered orthogonal to the vertical axis and the major longitudinal length of the nail;
   a first locking screw and a second locking screw;
   each of the first locking screw and the second locking screw are secured near one end of the nail to form an architecture having a substantial triangular shape;
   a first reinforcing screw being releasably mounted along the major longitudinal length of the nail;
   wherein the first locking screw includes
      a proximal end removably engaged with the nail, and
      a distal end having a threaded outer surface;
   wherein the second locking screw includes
      a proximal end removably engaged with the nail, and
      a distal end removably engaged with the proximal end of the first locking screw; and
   a second reinforcing screw abutted against the proximal end of the second locking screw;
   wherein each of the first locking screw, the second locking screw, the first reinforcing screw and the second reinforcing screw is registered non-perpendicular to the vertical axis;
   wherein each of the first locking screw, the second locking screw, the first reinforcing screw and the second reinforcing screw is registered non-parallel to the horizontal axis.

2. The surgical implant device according to claim 1, wherein the second reinforcing screw is releasably mounted along the major longitudinal length of the nail between the first reinforcing screw and the second locking screw.

3. The surgical implant device according to claim 1, wherein a major longitudinal length of the second locking screw has a smooth, continuous and uninterrupted outer surface beginning from the proximal end thereof and terminating adjacent to the distal end thereof.

4. The surgical implant device according to claim 3, wherein the distal end of the second locking screw has a threaded outer surface engaged with the threaded outer surface of the distal end of the first locking screw.

5. The surgical implant device according to claim 4, wherein the threaded outer surface of the distal end of the first locking screw is threadably engaged directly with the threaded outer surface of the distal end of the second locking screw.

6. The surgical implant device according to claim 5, wherein the second reinforcing screw has a proximal end directly engaged with the proximal end of the second locking screw.

7. The surgical implant device according to claim 6, wherein the proximal end of the second locking screw has a smooth and continuous outer surface and the proximal end of the second reinforcing screw has a smooth and continuous outer surface directly engaged therewith.

8. The surgical implant device according to claim 1, wherein the nail has an end cap at said one end and a convex distal taper at another end of said nail.

9. The surgical implant device according to claim 1, wherein the first locking screw may be in the form of lag screw.

10. The surgical implant device according to claim 1, wherein the threaded outer surface of the distal end of the second locking screw directly contacts the threaded outer surface of the distal end of the first locking screw.

11. The surgical implant device according to claim 1, wherein the first reinforcing screw is disposed through one of a plurality of holes in the nail, and the hole is in the form of an oval-shaped slot.

12. The surgical implant device according to claim 1, wherein the second reinforcing screw is disposed through one of a plurality of holes in the nail, and the hole is in the form of round-shaped hole.

13. The surgical implant device according to claim 1, wherein the first reinforcing screw may be in the form of shaft derotation screw.

14. The surgical implant device according to claim 1, wherein the second reinforcing screw is in the form of a subtrochanteric screw.

15. A method of implanting a surgical implant device into a fractured bone, the bone having two or more fragments due to the fracture, the method comprising:
providing a pin,
inserting the pin partially into one of the fragments of the bone,
using the pin to reduce the fracture by re-engaging the fragment with the corresponding fragment,
drilling a hole through the fragment and partially into the corresponding fragment,
providing a nail having several holes therein,
inserting the nail into the drilled hole in the fragments,
providing a first locking screw and a second locking screw,
providing an installing apparatus,
disposing each of the first locking screw and second locking screw through one of the holes by means of the installing apparatus and extending such that both of the screws engage each other at a position so as to form an architecture having substantial triangular shape,
providing a first reinforcing screw, and
disposing the first reinforcing screw through one of the holes of the nail by means of the installing apparatus;
providing a second reinforcing screw, and
disposing the second reinforcing screw through one of the holes of the nail between the first reinforcing screw and the second locking screw by means of the installing apparatus;
wherein the first locking screw includes
a proximal end removably engaged with the nail, and
a distal end having a threaded outer surface;
wherein the second locking screw includes
a proximal end removably engaged with the nail, and
a distal end removably engaged with the proximal end of the first locking screw; and
a second reinforcing screw abutted against the proximal end of the second locking screw;
wherein each of the first locking screw, the second locking screw, the first reinforcing screw and the second reinforcing screw is registered non-perpendicular to the vertical axis;
wherein each of the first locking screw, the second locking screw, the first reinforcing screw and the second reinforcing screw is registered non-parallel to the horizontal axis.

* * * * *